Figure 1:
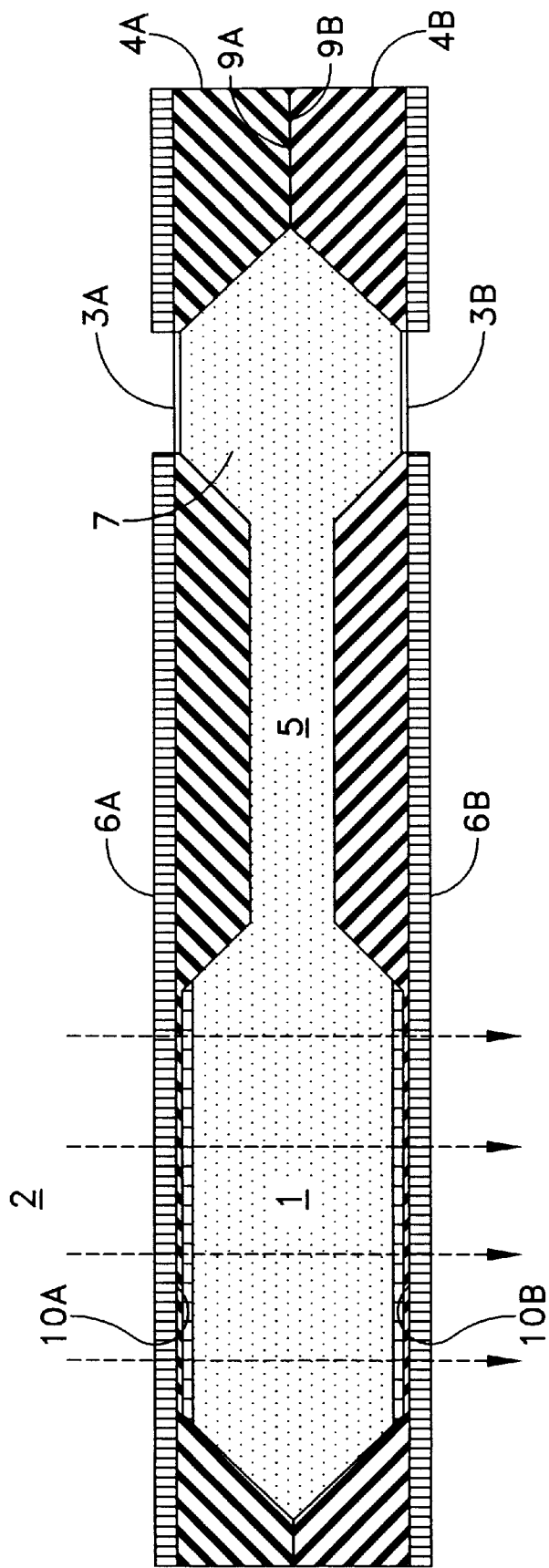

United States Patent [19]
Bernstein et al.

[11] Patent Number: 6,082,178
[45] Date of Patent: Jul. 4, 2000

[54] PHOTOACOUSTIC GAS DETECTOR

[75] Inventors: Ralph Bernstein, Nadderudlia; Per A. Øhlckers, Grønsudveien; Alain Ferber, Kirkeveien, all of Norway

[73] Assignee: Leiv Eiriksson Nyfotek AS, Trondheim, Norway

[21] Appl. No.: 08/875,883

[22] PCT Filed: Feb. 2, 1996

[86] PCT No.: PCT/NO96/00024

§ 371 Date: Dec. 5, 1997

§ 102(e) Date: Dec. 5, 1997

[87] PCT Pub. No.: WO96/24831

PCT Pub. Date: Aug. 15, 1996

[30]     Foreign Application Priority Data

Feb. 10, 1995 [NO]   Norway ..................................... 950505

[51] Int. Cl.[7] .................................................. G01N 21/00
[52] U.S. Cl. ............................................. 73/24.02; 73/579
[58] Field of Search ................................ 73/24.02, 61.75, 73/579; 250/343, 252.1, 352, 338.5, 339.13; 356/432

[56]               References Cited

U.S. PATENT DOCUMENTS

| | | | |
|---|---|---|---|
| H651 | 7/1989 | Davis et al. ........................... | 250/343 |
| 4,412,445 | 11/1983 | Spellicy ....................................... | 73/24 |
| 4,598,201 | 7/1986 | Fertig et al. ............................ | 250/352 |
| 4,622,845 | 11/1986 | Ryan et al. ................................. | 73/24 |
| 4,740,086 | 4/1988 | Oehler et al. ........................... | 356/432 |
| 5,668,303 | 9/1997 | Giesler et al. .......................... | 73/24.06 |
| 5,747,808 | 5/1998 | Wong ....................................... | 250/343 |
| 5,841,017 | 11/1998 | Baraket et al. ........................... | 73/1.59 |
| 5,866,800 | 2/1999 | Park et al. .............................. | 73/31.06 |
| 5,869,749 | 2/1999 | Bonne et al. ........................... | 73/24.02 |

*Primary Examiner*—Harshad Patel
*Attorney, Agent, or Firm*—Duane, Morris & Heckscher

[57]               ABSTRACT

A photoacoustic detector including a chamber (1) for receiving the gas, a path for pulsed or modulated IR radiation (2) into, through and out of the chamber, and a pressure sensor (3A–B) adapted to measure pressure changes in the chamber caused by the applied IR radiation. The chamber is formed by joining together at least two major semiconductor elements, in particular, silicon or quartz elements (4A–B) made in planar technology. At least a first element from a major surface (9A–B) has an etched recess which constitutes a substantial proportion of the volume of the chamber. At least one of the elements is provided with a membrane for the pressure sensor, and the space (7) in front of the membrane communicates with the chamber.

14 Claims, 3 Drawing Sheets

PHOTOACOUSTIC GAS DETECTOR

Photoacoustic techniques are based on a heat effect which is known as the photothermal effect. These techniques utilize the principle that absorbed radiation energy, in particular from infra-red (IR) radiation results in pressure variations in a given volume of gas, the pressure variations being proportional to the absorbed amount of energy. These pressure variations can then be detected by means of a sensitive pressure sensor.

This invention is directed to a photoacoustic gas detector comprising a chamber for receiving the gas or gas mixture concerned, a path for pulsed or modulated IR radiation into, through, and out of the chamber, and a pressure sensor adapted to measure pressure changes in the chamber caused by applied IR radiation.

Examples of known uses of such photoacoustic techniques are found, inter alia, in patent publication US-H651 and in an article by C. F. Dewey Jr, R. D. Kamm, and C. E. Hackett: Acoustic amplifier for detection of atmospheric pollutants, Appl. Phys. Lett., Vol. 23, No. 11, December 1973.

The present invention is aimed at substantial improvements in a photoacoustic gas detector as referred to above, by taking as a starting point a design based on semiconductor materials, in particular silicon or quartz elements as being for example commonly employed within the semiconductor technology. What is novel and specific in the gas detector according to the invention consists thus, in the first place in that the chamber for the gas or gas mixture is formed by joining together at least two semiconductor elements, in particular silicon or quartz elements manufactured by planar technology, whereby at least a first element from a major surface has an etched recess which constitutes a substantial portion of the volume of the chamber.

In order to provide a measuring signal corresponding to the membrane oscillations as a result of the pressure changes in the chamber, various principles can be contemplated, for example a capacitive measurement principle. Such principles and techniques are well known in connection with silicon pressure sensors and microphones or the like, and will not be discussed further here.

The design and manufacture of photoacoustic gas sensors on the basis of silicon or quartz micromechanics involve a number of substantial advantages. Such gas sensors are cheap in production, and with advantage can have one or more membranes formed as an integrated structure in one or more of the elements being joined together, so as to form the gas chamber. In most embodiments according to the invention planar technology will be utilized in an optimal way when each of the elements has a substantially plate-like shape.

Silicon and quartz are materials being well suited for the manufacture of photoacoustic gas sensors, among other things because they are transparent to IR radiation. Quartz has somewhat varying transmission properties for IR radiation depending upon the wavelength. It may also be possible to employ other semiconductor materials, for example semiconductor materials of the III–V semiconductor type, in gas detectors according to the present invention.

Another advantage has to do with the small dimensions being possible with such a gas detector, so that the chamber volume for the gas can be made very small. Accordingly the sensitivity of the detector is improved. Moreover the small chamber dimensions also mean that it will be easy to keep the temperature under control and the same applies to the pressure of the gas in the chamber. Not less important in some Uses, is this factor when the gases to be handled and measured are toxic or for other reasons should or can be present only in small amounts for the measurement of interest here.

The planar technology mentioned, which constitutes a substantial prerequisite for the invention, in general makes possible the formation or application of various layers or coatings in the gas detector structure in view of different effects and purposes, as will appear also from the following description.

In addition to utilization for gas measurement, which is in the first place discussed above, such a photoacoustic gas detector can also be employed as a locking device for a laser line, for example in advanced communications systems based on optical fibres.

Figure 2:
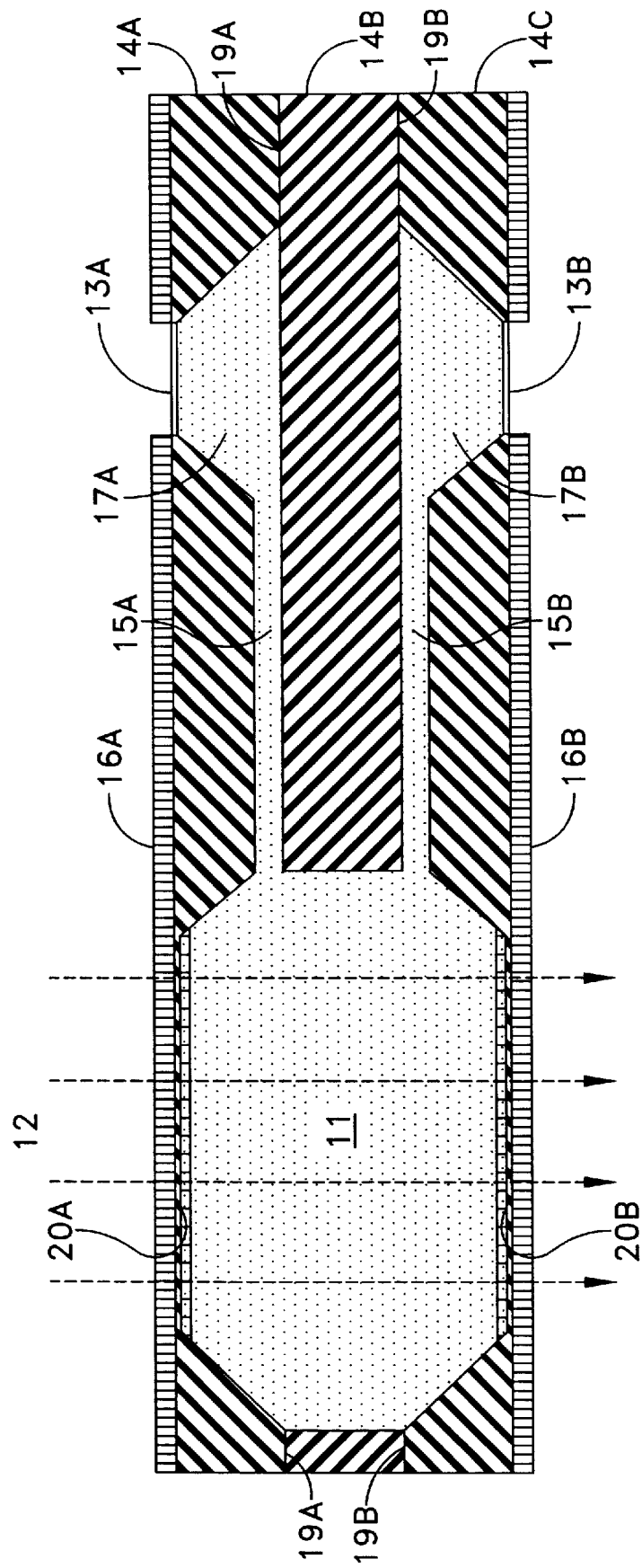
Figure 3:
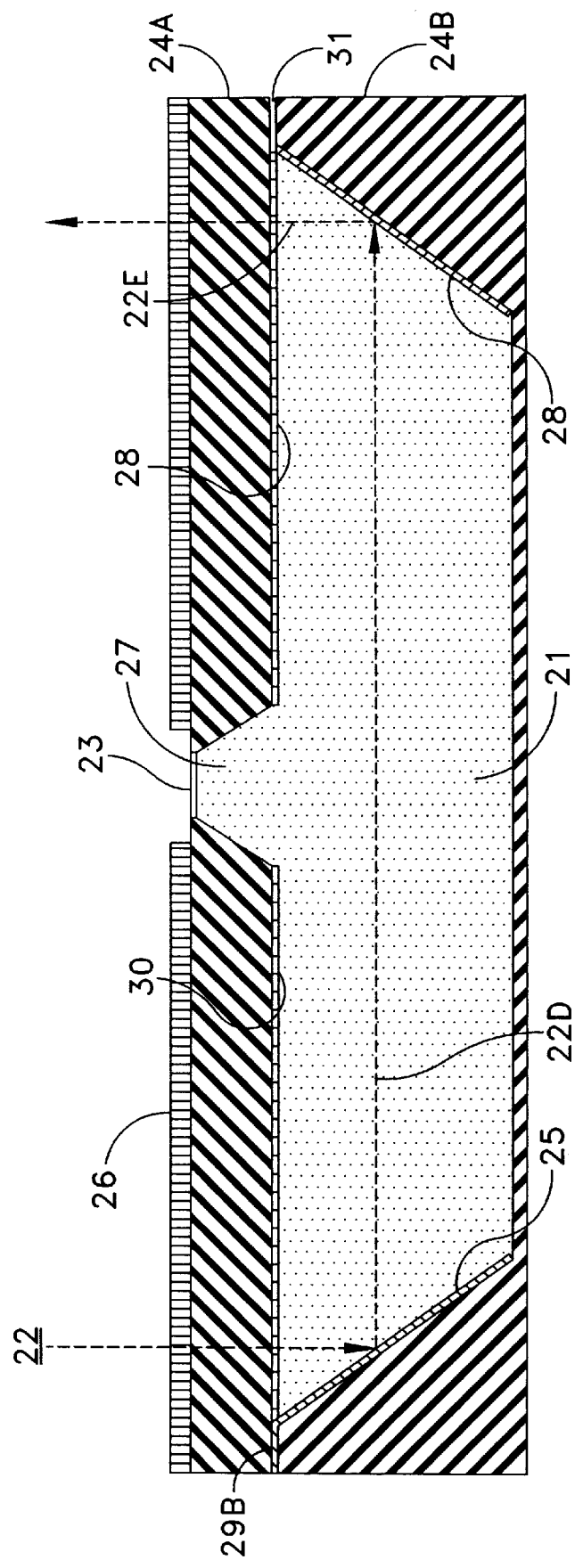

In the following description the invention will be explained more closely with reference to the drawings, wherein:

FIG. 1 in schematical cross-section shows an example of a first embodiment of the gas detector according to the invention, FIG. 2 in a corresponding manner shows an example of a second embodiment of the gas detector according to the invention, and FIG. 3 shows a third example of an embodiment of the gas detector according to the invention.

At the outset it is emphasized here that the figures of the drawings are of a purely fundamental and schematic character, whereby in particular the relative dimensions being shown, can deviate, possibly very significantly, from the dimensional relationships in corresponding gas detectors manufactured in practice.

The embodiment of FIG. 1 is based on the assembly of two silicon or quartz elements 4A and 4B, having preferrably a pronounced plate shape with outer surfaces which are to a substantial degree coated with an anti-reflecting coating 6A and 6B respectively. Plate element 4A has also an opposite or internal major surface 9A adapted to engage and be joined to a corresponding internal major surface 9B on plate element 4B. By this join there is obtained a hermetic seal between elements 4A and 4B around the whole perifery of the component. Methods for such joining are well known within planar technology.

The interior cavity formed by joining the two plate elements 4A and 4B primarily comprises a chamber 1 adapted to receive the gas or gas mixture concerned, which is adapted to be influenced by pulsed or modulated IR radiation 2. In this example it is envisaged that this radiation is applied directly through the thickness dimension of the gas detector so that a significant or substantial proportion of the gas in chamber 1 will be influenced by the IR radiation. Its absorption by the gas causes the gas to be subjected to pressure variations corresponding to the pulsing or modulation of the IR radiation.

Chamber 1 has been formed by etching, in a manner known per se, from the respective major surfaces 9A and 9B of plate elements 4A and 4B before these are joined together.

In a corresponding way there is formed a common space 7 in association with membranes 3A and 3B, which serve to convert the pressure variations in the gas, during measurement or detection, into output signals, being preferrably electrical signals, for further employment in the measurement system or the like concerned. The space 7 inside the membranes 3A and 3B communicate with chamber 1 through a passage 5 which can also be formed by etching from the inner surface of one or both plate elements 4A and 4B, in a corresponding way as chamber 1 and space 7.

According to an advantageous embodiment the pair of membranes 3A and 3B by utilizing planar technology are formed as integrated structures in the corresponding plate element 4A or 4B respectively. Such integrated manufacture of suitable structures is very convenient in planar technology, as will be obvious to experts within the field. This manufacturing method additionally involves an advantageous utlization of planar technology for producing gas detector components according to the invention, in a rational and efficient manner. Thereby there is also obtained a robust structure which can at the same time have very accurate dimensions and besides is well suited for capacitive or other conversion of the membrane excursions into desired measuring or output signals.

It is obvious that it could be sufficient with only one membrane in such a gas detector, in order to obtain the desired measuring signal. A structure having two membranes 3A and 3B facing oppositely as in FIG. 1, may however, as known per se, have a favourable equalizing effect on external noise that may be present, as such external mechanical noise through the sensor structure will influence the two membranes in different ways, whereas the pressure variations from chamber 1 will have an equal influence on the two membranes.

As shown in the drawing it will normaly not be practical to apply an anti-reflecting coating on the two membranes 3A and 3B. On the other hand it may be advantageous in some cases to employ anti-reflecting coatings not only externally as at 6A and 6B in FIG. 1, but also on some surfaces 10A and 10B in FIG. 1 and 20A and 20B in FIG. 2, in the internal cavity 1,5 or 7 in such a gas detector.

As known per se from the article referred to at the beginning above, it can be an advantage if the chamber 1 with the gas or gas mixture concerned received in it, is adapted to constitute an acoustic resonance chamber, the applied IR radiation 2 being modulated with frequencies coinciding with the natural frequencies of the chamber. It will be realized that both the volume and the shape of the actual chamber 1 as well as passage 5 and space 7 which communicate with the chamber, contribute to determining this acoustic resonance, i.e. the natural frequencies of the chamber.

As an alternative or addition to such chamber resonance it is possible and advantageous in certain embodiments, to design the membrane or membranes 3A and 3B such that this or these are resonant, whereby the applied IR radiation corresponding completely to what is discussed immediately above, is modulated with frequencies coinciding with one of the membranes natural frequencies.

The embodiment of FIG. 2 differs from the one in FIG. 1 primarily by being composed of three plate elements 14A, 14B and 14C, whereby elements 14A and 14B can be considered to correspond to elements 4A and 4B respectively in FIG. 1, whereas element 14C is an intermediate plate element which, primarily serves to give a relative increase of the volume of the chamber 11. Thus as will be seen from FIG. 2 plate element 14C has a completely through-going opening for chamber 11, and elements 14A and 14B have corresponding recesses etched away as in elements 4A and 4B in FIG. 1. The resulting, comparatively larger chamber 11 communicates with relatively smaller, separate spaces 17A and 17B in front of membranes 13A and 13B respectively, in either plate element 14A and 14B. Space 17A communicates with chamber 11 through a relatively narrow passage 15A, whereas space 17B correspondingly communicates with chamber 11 through a passage 15B. Passages 15A and 15B can here with advantage be etched away from the inner major surface 19A of element 14A, and major surface 19B of element 14B respectively. In this way the manufacture of the intermediate plate element 14C will be somewhat simplified. In a corresponding manner as in the embodiment of FIG. 1, the three plate elements are here joined at the inner major surfaces 19A/19C1 and 19B/19C2 respectively. Also in this embodiment there are applied anti-reflection coatings 16A and 16B. The manner of operation of this form of gas detector according to the invention will to a high degree be analogous to what is explained in connection with FIG. 1, including possible resonance effects. The advantage of the embodiment in FIG. 2 in the first place consists in that spaces 17A and 17B in front of the membranes can be designed with relatively smaller volumes, so that the pressure variations in chamber 11 more effectively can give rise to corresponding membrane excursions. In this connection it is also significant that passages 15A and 15B are relatively narrow, i.e. they represent small gas volumes. On the other hand it is also obvious that the embodiment of FIG. 2 is somewhat more complicated and expensive than the one in FIG. 1.

In the third embodiment as shown in FIG. 3, there are again two plate elements 24A and 24B, and a chamber 21 being here formed by etching out a recess only in plate element 24B. This embodiment is well suited for laser IR sources having small beam cross-sectional areas. Moreover only plate element 24A is provided with a membrane 23, with a space or passage 27 in front of the membrane, so that through-communication with chamber 21 is obtained, so that pressure variations in the chamber shall influence the membrane 23. The recess for passage 27 is etched into plate element 24 from its inner major surface 29A. Along the edges this major surface is joined to the inner major surface 29B of element 24B. The outer surface of element 24A is provided with an anti-reflection coating 26.

In this embodiment the path for IR radiation 22 through the gas detector, i.e. chamber 21, is arranged somewhat differently from FIGS. 1 and 2, since two reflecting surface portions 25 and 28 internally in chamber 21 serve to deflect the radiation so that it will follow a path 22D through chamber 21 and exit from the chamber at 22E as illustrated. In certain cases such a radiation path can be an advantage in practice. It is obvious that such a chamber 21 can be designed in various ways with the possibility of varying the arrangement of internal reflecting portions or coatings 30 so as to obtain desired paths or trajectories of the applied IR radiation. In FIG. 3 the inclined surfaces being provided with mirror coatings 25 and 28 are arranged at suitable angles, formed by the etching of the recess for chamber 21 in element 24B. In this connection angles of 45° or 54,7° can be of interest in practice.

With respect to the embodiments of FIGS. 1 and 2 it has not been stated how the chambers 1 and 11 as described, are filled with the gas or gas mixture concerned. It is obvious, however, that during manufacture of the gas detectors or when these shall be made ready for measurement, gas filling must take place, for example through suitable orifices, which can then be sealed so that the gas concerned will be permanently incorporated in the detector. This is a manner of use being of interest when the gas detector concerned is intended for measurement or detection of a particular gas or gas mixture. In other uses it can be of significance to let the gas or gas mixture concerned, flow through the gas detector more or less continuously. Quite schematically in FIG. 3 there is shown an inlet orifice 31 for this purpose. Obviously a corresponding outlet orifice must also be provided in order that through-flow shall be able to take place.

The description above with reference to the figures of drawings essentially serves to explain the fundamental structure of gas detectors according to the invention, in a rather schematic and elementary way. In practical embodiments of such detector components there may be contemplated various modifications and details, which can be convenient in the individual uses being of interest. Thus, various types of light sources can be employed, such as lasers, thermal sources and LED light sources. Such light sources can also be disposed directly on the surface of the gas detector more or less as an integrated part of the total structure. Moreover these embodiments can have a specific window or windows for the applied IR radiation, even if the main materials silicon or quartz as well as the anti-reflecting coatings discussed, are transparent to IR radiation.

The angle of incidence of radiation can also be varied in relation to the normal incidence being illustrated in the figures of drawings, whereby the main consideration at this point usually is that as much as possible of the IR radiation from the source shall enter into the detector and through the gas chamber inside it. For this light or radiation input it is also possible to take advantage of the Brewster angle.

As a further detail in connection with the radiation path, there can be provided a separate detection device for the IR radiation coming out of the gas detector. The purpose of such detection could be to check the radiation through-put and/or to perform calibration.

With respect to the membranes a capacitive principle is mentioned above for obtaining an electrical output signal, and here are additionally mentioned the piezo-resistive or piezo-electric and optical effect or "tunnel" effect, which can also be utilized.

As a practical sealing method for joining the plate elements described, anodic sealing is well suited. For the purpose of obtaining long term stability of the finished gas detector with its filling of a gas or a gas mixture, suitable and known coating techniques can be employed for treatment of in particular the internal surfaces which surround the cavities described, where the gas chamber itself constitutes a substantial volume.

In practical embodiments of the gas detector there may be a question of rather small dimensions, such as a total thickness of the assembled plate elements in the order of magnitude of 1 mm, whereas the area extension of the elements can be substantially larger. For example the membranes described can have a surface area of 3×3 mm. These dimensional relationships are quite reasonable and without problems when the design is based on planar technology such as described.

What is claimed is:

1. A photoacoustic detector for a gas or a gas mixture, comprising a chamber for receiving the gas or gas mixture concerned, a path for pulsed or modulated IR radiation to pass into, through, and out of the chamber, and a pressure sensor adapted to measure pressure variations in the chamber caused by the IR radiation, wherein the chamber is formed by joining together at least two semiconductor elements manufactured in planar technology, at least one of the elements having one major surface with an etched recess which constitutes a substantial proportion of the volume of the chamber, and at least one of the elements being provided with a membrane for the pressure sensor and a space in front of the membrane in communication with the chamber.

2. The detector according to claim 1, wherein each of said elements has a substantially plate-like shape.

3. The detector according to claim 1, wherein the membrane is formed as an integrated structure of the element.

4. The detector according to claim 1, wherein the chamber is adapted to be closed upon being filled with the gas or gas mixture for the purpose of detecting or measuring a substantially similar type of gas outside the chamber.

5. The detector according to claim 1, wherein the chamber has orifices for flowthrough of the gas to be detected or measured.

6. The detector according to claim 1, further comprising at least one reflecting portion adapted to influence the IR radiation being applied.

7. The detector according to claim 6, wherein the reflecting portion is provided on at least one internal surface in the chamber.

8. The detector according to claim 1, further comprising at least one anti-reflection coating applied externally to at least one of the elements of the chamber.

9. The detector according to claim 8, further comprising at least one anti-reflection coating applied to an internal surface in the chamber.

10. The detector according to claim 1, wherein the chamber, when the gas or gas mixture is received therein, is structured to have acoustic resonance associated with modulation of the applied IR radiation with frequencies coinciding with the acoustic resonance in the chamber.

11. The detector according to claim 1, wherein the membrane, when the gas or gas mixture is received in the chamber, is resonant, in association with modulation of the applied IR radiation with frequencies coinciding with the membrane resonance.

12. The detector according to claim 1, wherein the semiconductor elements are selected from the group consisting of silicon or quartz.

13. The detector according to claim 1 wherein a first one of said at least two semiconductor elements is provided with an etched recess constituting said chamber, and a second one of said at least two semiconductor elements is provided with said membrane, wherein said space in front of said membrane communicates with said chamber through a passage etched from said major surface of said second element.

14. The detector according to claim 1 wherein a first one of said at least two semiconductor elements is provided with an etched recess constituting said chamber, and a second one of said at least two semiconductor elements is provided with said membrane, wherein said space in front of said membrane communicates with said chamber through a recess etched from said major surface of said second element.

* * * * *